(12) United States Patent
Woolfson et al.

(10) Patent No.: US 7,507,790 B2
(45) Date of Patent: Mar. 24, 2009

(54) FIBER-SHAPING PEPTIDES CAPABLE OF INTERACTING WITH SELF-ASSEMBLING PEPTIDES

(75) Inventors: Derek Woolfson, Bristol (GB); Maxim Gennadievich Ryadnov, Bristol (GB)

(73) Assignee: University of Sussex, Falmer, Brighton, Sussex (GB)

(*) Notice: Subject to any disclaimer, the term of this patent is extended or adjusted under 35 U.S.C. 154(b) by 0 days.

(21) Appl. No.: 10/526,367

(22) PCT Filed: Sep. 8, 2003

(86) PCT No.: PCT/GB03/03900

§ 371 (c)(1),
(2), (4) Date: Nov. 30, 2005

(87) PCT Pub. No.: WO2004/022584

PCT Pub. Date: Mar. 18, 2004

(65) Prior Publication Data

US 2006/0155112 A1 Jul. 13, 2006

(30) Foreign Application Priority Data

Sep. 6, 2002 (GB) ................................. 0220805.6

(51) Int. Cl.
*A61K 38/00* (2006.01)
*A61K 51/00* (2006.01)
*A61M 36/14* (2006.01)
*C07K 5/00* (2006.01)
*C07K 7/00* (2006.01)
*C07K 10/00* (2006.01)
*C07K 17/00* (2006.01)

(52) U.S. Cl. .......................... 530/325; 514/2; 424/1.69; 530/323

(58) Field of Classification Search ........................ None
See application file for complete search history.

(56) References Cited

U.S. PATENT DOCUMENTS 5,955,343 A    9/1999  Holmes et al.

FOREIGN PATENT DOCUMENTS

WO    WO 01 21646 A    3/2001
WO    WO 0121646    *  3/2001

OTHER PUBLICATIONS

Hartgerink et al. "Self-Assembly and Mineralization of Peptide-Amphiphile Nanofibers" Nov. 2001, Science vol. 294 pp. 1684-1688.*
Pandya M J et al: "Sticky-end assembly of a designed peptide fiber provides insight into protein fibrillogenesis ." Biochemistry. United States Aug. 1, 2000, vol. 39, No. 30, pp. 8728-8734, XP002264453 ISSN: 0006-2960. The documents discloses the SAF peptides, such as the sequences disclosed in claim 30, see Exp. Procedure and Fig. 1-2.
Holmes T C et al: "Extensive neurite outgrowth and active synapse formation on self-assembling peptide scaffolds." Proceeding of the National Academy of Sciences of the United States of America. United States Jun. 6, 2000, vol. 97, No. 12, pp. 6728-6733, XP002264454 ISSN: 0027-8424. See Mat. and Methods p. 6729, and pp. 6730-6731 last paragraph of p. 6733.
Padilla Jennifer E et al: "Nanohedra: Using symmetry to design self assembling protein cages, layers, crystals, and filaments" Proceedings of the National Academy of Sciences of the United States, vol. 98, No. 5, Feb. 27, 2001, pp. 2217-2221, XP002264456 Feb. 27, 2001 ISSN: 0027-8424.
Zhang Shuguang et al: "Design of nanostructured biological materials through self-assembly of peptides and proteins." Current Opinion in Chemical Biology. England Dec. 2002,vol. 6, No. 6, Dec. 2002, pp. 865-871, XP002264457 ISSN: 1367-5931.
Moll Dieter et al: "S-layer-streptavidin fusion proteins as template for nanopatterned molecular arrays." Proceedings of the National Academy of Sciences of the United States, vol. 99, No. 23, Nov. 12, 2002, pp. 14646-14651, XP002264455 Nov. 12, 2002 ISSN: 0027-8424.
Ryadnov Maxim G et al: "Engineering the morphology of a self-assembling protein fibre." Nature Materials. England May 2003, vol. 2, No. 5, pp. 329-332, XP001156809 ISSN: 1476-1122.

* cited by examiner

*Primary Examiner*—Cecilia Tsang
*Assistant Examiner*—Maury Audet
(74) *Attorney, Agent, or Firm*—Banner & Witcoff, Ltd.

(57) ABSTRACT

The present invention relates to a fiber-shaping peptides that are capable of interacting with self-assembling peptides to form protein structures. The present invention also relates to methods of forming protein structures using the fiber-shaping peptides of the present invention.

18 Claims, 6 Drawing Sheets

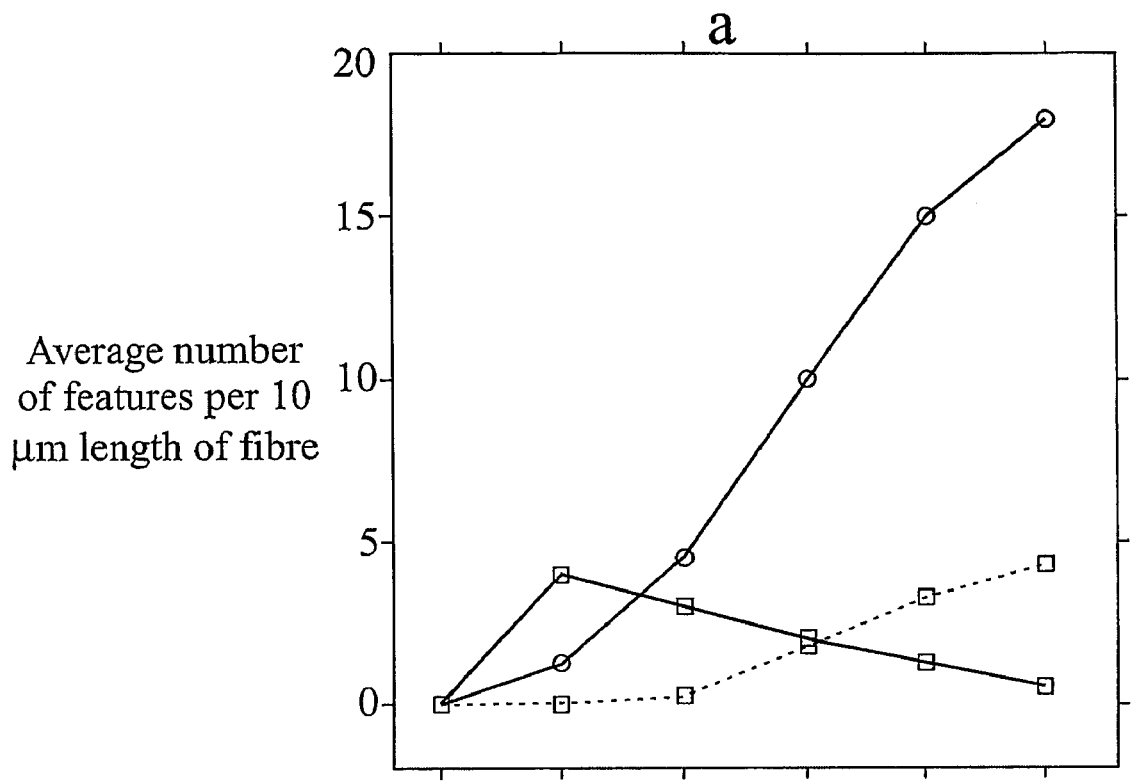
*Fig. 3*
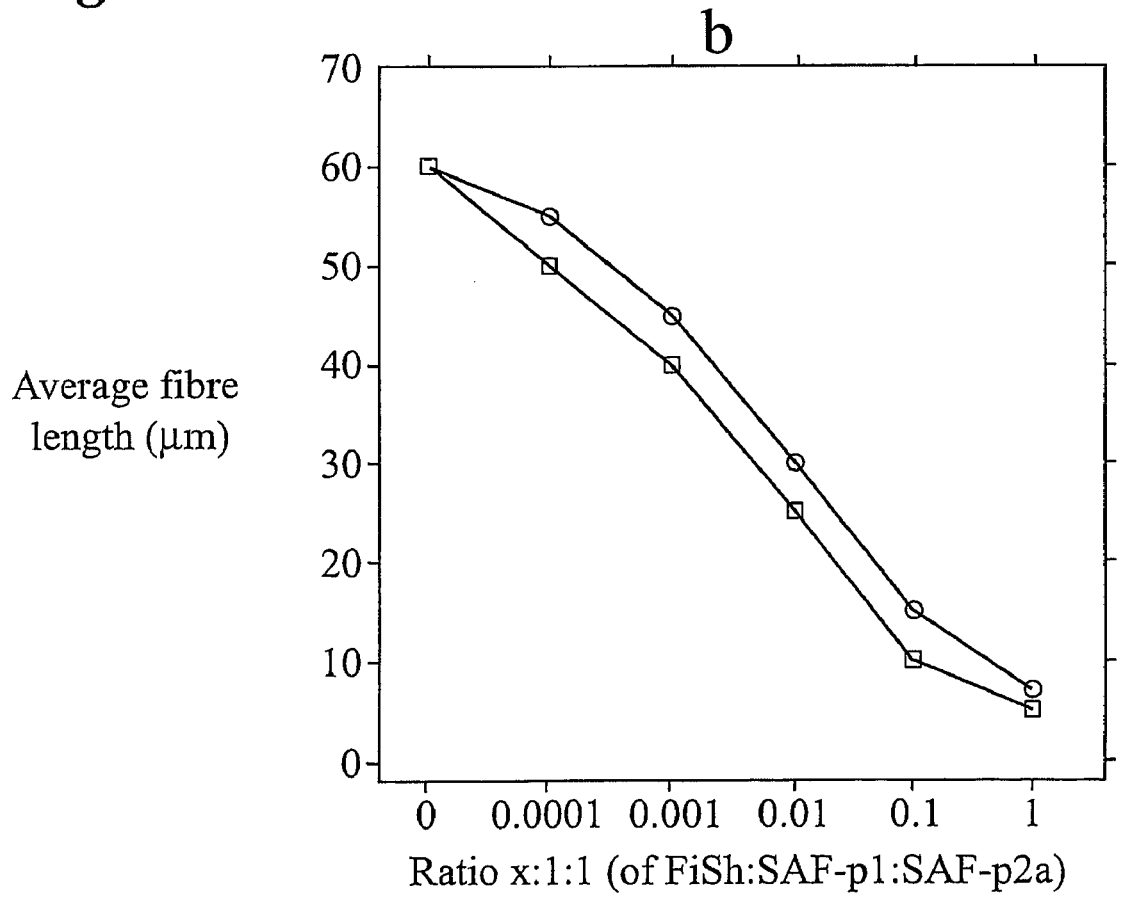

SEQUENCE LISTING

```
<160> NUMBER OF SEQ ID NOS: 10

<210> SEQ ID NO 1
<211> LENGTH: 28
<212> TYPE: PRT
<213> ORGANISM: Artificial Sequence
<220> FEATURE:
<223> OTHER INFORMATION: peptide SAF-p1

<400> SEQUENCE: 1

Lys Ile Ala Ala Leu Lys Gln Lys Ile Ala Ser Leu Lys Gln Glu Ile
 1               5                  10                  15

Asp Ala Leu Glu Tyr Glu Asn Asp Ala Leu Glu Gln
            20                  25

<210> SEQ ID NO 2
<211> LENGTH: 28
<212> TYPE: PRT
<213> ORGANISM: Artificial Sequence
<220> FEATURE:
<223> OTHER INFORMATION: peptide SAFp2a

<400> SEQUENCE: 2

Lys Ile Arg Arg Leu Lys Gln Lys Asn Ala Arg Leu Lys Gln Glu Ile
 1               5                  10                  15

Ala Ala Leu Glu Tyr Glu Ile Ala Ala Leu Glu Gln
            20                  25

<210> SEQ ID NO 3
<211> LENGTH: 17
<212> TYPE: PRT
<213> ORGANISM: Artificial Sequence
<220> FEATURE:
<223> OTHER INFORMATION: fiber shaping peptide
<221> NAME/KEY: VARIANT
<222> LOCATION: (14)...(16)
<223> OTHER INFORMATION: Xaa is bAla

<400> SEQUENCE: 3

Lys Ile Arg Arg Leu Lys Gln Lys Asn Ala Arg Leu Lys Xaa Xaa Xaa
 1               5                  10                  15

Lys

<210> SEQ ID NO 4
<211> LENGTH: 16
```

```
<212> TYPE: PRT
<213> ORGANISM: Artificial Sequence
<220> FEATURE:
<223> OTHER INFORMATION: fiber-shaping peptide
<221> NAME/KEY: VARIANT
<222> LOCATION: (14)...(16)
<223> OTHER INFORMATION: xaa is bAla

<400> SEQUENCE: 4

Lys Ile Arg Arg Leu Lys Gln Lys Asn Ala Arg Leu Lys Xaa Xaa Xaa
 1               5                  10                  15

<210> SEQ ID NO 5
<211> LENGTH: 18
<212> TYPE: PRT
<213> ORGANISM: Artificial Sequence
<220> FEATURE:
<223> OTHER INFORMATION: fiber shaping peptide
<221> NAME/KEY: VARIANT
<222> LOCATION: (2)...(4)
<223> OTHER INFORMATION: Xaa is bAla

<400> SEQUENCE: 5

Glu Xaa Xaa Xaa Glu Ile Ala Ala Leu Glu Tyr Glu Ile Ala Ala Leu
 1               5                  10                  15

Glu Gln

<210> SEQ ID NO 6
<211> LENGTH: 17
<212> TYPE: PRT
<213> ORGANISM: Artificial Sequence
<220> FEATURE:
<223> OTHER INFORMATION: fiber shaping petpide
<221> NAME/KEY: VARIANT
<222> LOCATION: (1)...(3)
<223> OTHER INFORMATION: Xaa is bAla

<400> SEQUENCE: 6

Xaa Xaa Xaa Glu Ile Ala Ala Leu Glu Tyr Glu Ile Ala Ala Leu Glu
 1               5                  10                  15

Gln

<210> SEQ ID NO 7
<211> LENGTH: 29
<212> TYPE: PRT
<213> ORGANISM: Artificial Sequence
<220> FEATURE:
<223> OTHER INFORMATION: peptide SAF-p2

<400> SEQUENCE: 7

Lys Ile Arg Ala Leu Lys Ala Lys Asn Ala His Leu Leu Lys Gln Glu
 1               5                  10                  15

Ile Ala Ala Leu Glu Gln Glu Ile Ala Ala Leu Glu Gln
                 20                  25

<210> SEQ ID NO 8
<211> LENGTH: 27
<212> TYPE: PRT
<213> ORGANISM: Artificial Sequence
<220> FEATURE:
<223> OTHER INFORMATION: self-assembling peptide

<400> SEQUENCE: 8

Ile Arg Arg Leu Lys Gln Lys Asn Ala Arg Leu Lys Gln Glu Ile Ala
 1               5                  10                  15

Ala Leu Glu Tyr Glu Ile Ala Ala Leu Glu Gln
```

-continued

```
                  20                  25

<210> SEQ ID NO 9
<211> LENGTH: 16
<212> TYPE: PRT
<213> ORGANISM: Artificial Sequence
<220> FEATURE:
<223> OTHER INFORMATION: peptide monomer unit
<221> NAME/KEY: VARIANT
<222> LOCATION: (14)...(16)
<223> OTHER INFORMATION: Xaa is bAla

<400> SEQUENCE: 9

Lys Ile Arg Arg Leu Lys Gln Lys Asn Ala Arg Leu Lys Xaa Xaa Xaa
  1               5                  10                  15

<210> SEQ ID NO 10
<211> LENGTH: 17
<212> TYPE: PRT
<213> ORGANISM: Artificial Sequence
<220> FEATURE:
<223> OTHER INFORMATION: peptide monomer unit
<221> NAME/KEY: VARIANT
<222> LOCATION: (1)...(3)
<223> OTHER INFORMATION: Xaa is bAla

<400> SEQUENCE: 10

Xaa Xaa Xaa Glu Ile Ala Ala Leu Glu Tyr Glu Ile Ala Ala Leu Glu
  1               5                  10                  15

Gln
```

FIBER-SHAPING PEPTIDES CAPABLE OF INTERACTING WITH SELF-ASSEMBLING PEPTIDES

This application is a National Stage application of co-pending PCT application PCT/GB2003/003900 filed 8 Sep. 2003, which was published in English language under PCT Article 21(2) on 18 Mar. 2004, and claims the benefit of the GB Application No. 0220805.6 filed 6 Sep. 2002.

The present invention relates to fibre-shaping peptides that are capable of interacting with self-assembling peptides to form protein structures. The present invention also relates to methods of forming protein structures using the fibre-shaping peptides of the present invention.

Biological assemblies provide inspiration for the development of new materials for a variety of applications (Holmes, Trends Biotechnol., 20, 16-21, 2002 and Yeates et al., Curr. Opin. Struct. Biol., 12, 464-470, 2002). The ability to realise this potential, however, is hampered by difficulties in producing and engineering natural biomaterials, and in designing them de novo. Recently, the inventors described a self-assembling system comprising two short, synthetic polypeptides (dubbed self-assembling peptides (also referred to as straights) herein), which combine to form extended fibres (see International Patent Application WO 01/21646 and Pandya et al., Biochemistry, 39, 8728-8734, 2000). The fibres described in WO 01/21646 are about 50 nm in diameter, and extend straight and without branching for tens to hundreds of microns. It is desirable to influence and to control fibre morphology.

Previously, the inventors applied the concept of sticky-end directed molecular assembly, which is well documented for the assembly of DNA, to peptides. This led to a self-assembling peptide fibre (SAF) system (Pandya et al., Biochemistry, 39, 8728-8734, 2000). The system comprises two short peptides (SAF-p1 and SAF-p2) of de novo design. The SAF-p1 and SAF-p2 sequences were based on accepted design principles for parallel, hetero-dimeric coiled coils, namely leucine zippers (Harbury et al., Science, 262, 1401-1407, 1993; O'Shea et al., Curr. Biol., 3, 658-667, 1993; Woolfson et al., Prot. Sci., 4, 1596-1607, 1995; Ciani et al., J. Biol. Chem., 277. 10150-10155, 2002). However, the SAF peptides were each designed with two distinct regions or sub-units: A and B in SAF-p1 and C and D in SAF-p2, respectively; where A complements D and B complements C. Thus, as depicted in FIG. 1a, co-assembly of the two peptides should lead to sticky-ended hetero-dimers, which should further assemble into fibres (see FIG. 1b). These design features were confirmed experimentally using a combination of spectroscopy, X-ray fibre diffraction and microscopy; although, interestingly, the fibres were thicker than originally anticipated. For instance, transmission electron microscopy (TEM) revealed that, when mixed in water and allowed to mature for short periods, the SAF peptides produced linear structures 40-50 nm in diameter that extended for many microns, FIG. 2a. Except for some rare examples where the fibres were bent, there was no evidence for non-linear or branched structures. More recently, the inventors redesigned SAF-p2 to make SAF-p2a, which combines with SAF-p1 more efficiently and produces fibres with significantly improved stability and internal order compared with the original design; otherwise, the appearance of the matured fibres was not altered.

U.S. Pat. No. 5,229,490 and International Patent Application No. WO 92/18528 are directed to branched peptides; however, the branched peptides do not interact with self-assembling peptides for form protein structures. The branched polypeptides are used to display antigens.

It would be of considerable interest to alter fibre size and morphology through rational design: for instance, such that specific fibres could be tailored and/or fibre assembly could be made to respond to patterned surfaces, or to cultures of growing cells. One possibility is to introduce special peptides (herein referred to as fibre-shaping peptides) that complement and assemble with the straight SAF building blocks (self-assembling peptides), but introduce discontinuities into the regularly repeating linear structure.

The present invention provides a fibre-shaping peptide comprising a hub and a plurality of peptide monomer units each being attached at one end thereof to the hub, wherein the free ends of at least 2 peptide monomer units are N-termini or C-termini, and each of the at least 2 peptide monomer units is capable of interacting with a subunit of a self-assembling peptide to form an overlapping staggered structure.

The fibre-shaping peptides of the present invention allow morphological changes to be made to protein fibres comprising self-assembling peptides. In particular, the fibre-shaping peptides allow one to incorporate branches, splits, kinks and bends in the protein fibres. By being able to incorporate such morphological changes in the protein fibres it is possible to generate a variety of protein structures, such as assemblies in general, including matrices, filters, networks, grids, scaffolds, etc.

As indicated above, the fibre-shaping peptide of the present invention comprises a hub to which peptide monomer units are attached. The peptide monomer units are attached covalently to the hub. The hub can be any molecule which has at least 2 derivatisable sites (so that it is possible to attach at least 2 peptide monomer units) and which does not prevent at least 2 peptide monomer units interacting with a sub-unit of a self-assembling peptide to form an overlapping staggered structure. It is further preferred that the hub has more than 2 derivatisable sites enabling the attachment of more than 2 peptide monomer units and/or the attachment of one or more active molecules. It is particularly preferred that the hub has 3 or 4 derivatisable groups.

In a preferred embodiment the fibre-shaping peptide comprises one or more active molecules attached to the hub. The active molecule can be any molecule that has a desired function provided it does not prevent at least 2 peptide monomer units interacting with a sub-unit of a self-assembling peptide to form an overlapping staggered structure. Suitable active molecules include an antibody molecule (i.e. a monoclonal antibody or functional part thereof, including Fab, Fv, F(ab')$_2$ fragments and single chain Fv fragments), a receptor, a ligand, an enzyme, an antigen, a label, a metal ion or a nucleic acid molecule. In a particularly preferred embodiment the active molecule is biotin. The biotin molecule can be used to bind streptavidin, which may be free or attached to a desirable molecule, such as a label or other active molecules. The active molecule may be used to bind a desired substance from a solution. For example, an antibody molecule may be used to bind the corresponding antigen. Alternatively, a receptor can be used to bind the corresponding ligand. When the active molecule is a nucleic acid, it can be used to bind transcription factors or even complementary nucleic acids. It is particularly preferred that the active molecule is an RGD based peptide. The RGD peptide can be used to isolate cells from a solution.

The hub is preferably one or more amino acids, more preferably 1 to 6 amino acids and most preferably 1 amino acid. In a preferred embodiment, the hub is lysine. When the hub is lysine, it is possible to attach 2 peptide monomer units via their C-terminus ends to the amino groups. A further peptide monomer unit or an active molecule can be attached to the carboxylic acid group.

In a further preferred embodiment the hub is glutamic acid. When the hub is glutamic acid, it is possible to attach 2 peptide monomer units via their N-terminus ends to the carboxylic acid groups. A further peptide monomer unit or an active molecule can be attached to the amino group.

Preferably the peptide monomer units and the functional molecules are linked to the hub via flexible linkers. The flexible linker may be any suitable linker. Preferably the flexible linker is composed of amino acids such as glycine, serine, alanine and β-alanine. It is particularly preferred that the flexible linker is a poly-β-alanine peptide comprising between 2 and 10 residues, more preferably about 3 to 5 residues. The flexible linker assists in allowing the peptide monomer units to easily interact with the self-assembling peptides and allows any functional molecules to exert their function.

The term "a peptide monomer unit" as used herein refers to a peptide that can interact with a sub-unit of a self-assembling peptide. In other words the peptide monomer unit is complementary to a sub-unit of a self-assembling peptide. The peptide monomer units of the fibre-shaping peptide interact with self-assembling peptides to form overlapping staggered structures which then self-assemble into a protein structure as described in WO 01/21646, and as shown in FIG. 1. The sub-unit of the self-assembling peptide is a region that specifically interacts with the peptide monomer unit. Generally, the sub-unit is at one end of the self-assembling peptides so that on interaction an overlapping staggered structure is formed. Preferably the peptide monomer units of the fibre-shaping peptide and the self-assembling peptides comprise a heptad and/or a hendecad repeat motif. It is also preferred that at least one of the peptide monomer units comprises an amino acid residue which is complementary to a residue in a sub-unit of the self-assembling peptide to encourage the fibre-shaping peptide and the self-assembling peptide to form a staggered parallel heterodimer. The amino acid residue in the peptide monomer unit may be any residue which can pair with a complementary amino acid in the sub-unit of the self-assembling peptide. Preferably the complementary amino acids are pairs of asparagines, arginines or lysines. It is also preferred that the complementary amino acids are at interfacial sites on the peptides. Preferably the complementary amino acids are in the "a" position within the heptad or hendecad repeat motif on the peptide monomer unit and in the sub-unit of the self-assembling peptide.

The fibre-shaping peptide of the present invention may comprise more than 2 peptide monomer units. It is preferred that the fibre-shaping peptide comprises 2 to 10 peptide monomer units, more preferably 2 to 5 peptide monomer units, most preferably 2 peptide monomer units. As indicated above, the number of peptide monomer units in the fibre-shaping peptide will depend on the number of derivatisable groups on the hub.

As indicated above, at least 2 of the peptide monomer units must have either free N-terminal ends or free C-terminal ends. By ensuring that the fibre-shaping peptide comprises 2 peptide monomer units having the same free ends (i.e. both C-terminal or both N-terminal ends), 2 self-assembling peptides are forced to converge leading to a discontinuity in the protein structure formed by the self-assembling peptides (see FIGS. 1c and d).

The term "self-assembling peptide" as used herein refers to a peptide that can interact with other self-assembling peptides to form a substantially linear structure, preferably a straight protein fibre. The self-assembling peptides preferably associate in a parallel and contiguous manner. Suitable self-assembling peptides are described in WO 01/21646. Preferably the self-assembling peptide comprises a heptad or hendecad repeat motif, wherein a pair of complementary amino acids residues on different self-assembling peptides encourage the self-assembling peptides to form a staggered parallel heterodimer coiled-coil. The complementary amino acid residues may be any residues which can form a pair. Preferably the complementary amino acids are pairs of asparagines, arginines or lysines. It is also preferred that the complementary amino acids are at interfacial sites on the peptides. Preferably the complementary amino acids are in the "a" position within the heptad or hendecad repeat motif in the self-assembling peptide.

It is particularly preferred that the self-assembling peptide has the sequence

NH$_3$-KIAALKQKIASLKQLIDALLYLNDALLQ-COOH (SAF-p1) (SEQ ID NO: 1)

or the sequence

NH$_3$-KIRRLKQKNARLKQLIAALLYLIAALLQ-COOH (SAF-p2a) (SEQ ID NO: 2).

The present invention also provides a self-assembling peptide having the sequence NH$_3$-KIRRLKQKNARLKQEIAALEYEIAALEQ-COOH (SAF-p2a) (SEQ ID NO: 2).

The standard single letter amino acid terminology is used in the sequences given in the present application.

The term "overhanging staggered structure" refers to a structure in which 2 peptides assemble to form a heterodimer having overhanging ends that are not interacting within the heterodimer.

The peptides of the present invention, including the fibre-shaping peptides and the self-assembling peptides are preferably between 15 and 100 amino acids in length, more preferably between 20 and 50 amino acids in length, most preferably about 30 amino acids in length. The peptides may comprise naturally occurring amino acids, synthetic amino acids and naturally occurring amino acids that have been modified.

The term "fibre" as used herein refers to a protein structure assembled from overlapping staggered structures interacting through the overhanging ends. A number of fibres may interact laterally thereby forming thicker fibres. It is particularly preferred that the term refers to a hetero-dimeric coiled coil structure.

The term "amino acid" as used herein refers to naturally occurring amino acids, synthetic amino acids and naturally occurring amino acids that have been modified.

In a preferred embodiment of the present invention the fibre-shaping peptide of the present invention has the formula:

$$(NH_3\text{-g(abcdefg)}_q\text{abcde-}(X)_m)_n\text{—Y—}((X)_m\text{-Z})_p \quad (I)$$

or $$(Z\text{-}(X)_m)_p\text{—Y—}((X)_m\text{-g(abcdefg)}_q\text{abcdef-COOH})_n \quad (II)$$

wherein abcdefg is a heptad repeat motif;
X is a flexible linker;
Y is a hub;
Z is a functional molecule;
$q$ is 1 to 15;
$m$ is 0 or 3;
$n$ is 2 to 10; and
$p$ is 0 to 4.

In a particularly preferred embodiment of the present invention the fibre-shaping peptide of the present invention has the formula:

$$(NH_3\text{-}g(abcdefg)_q abcde\text{-}(X)_m)_n\text{-}Y\text{-}((X)_m\text{-}Z)_p \quad (I)$$

or $$(Z\text{-}(X)_m)_p\text{-}Y\text{-}((X)_m\text{-}g(abcdefg)_q abcdef\text{-}COOH)_n \quad (II)$$

wherein abcdefg is a heptad repeat motif;
X is a flexible linker;
Y is a hub;
Z is a functional molecule;
$q$ is 1 to 15;
$m$ is 0 or 1;
$n$ is 2 to 10; and
$p$ is 0 to 4.

Preferably, X is a flexible linker as defined above.
Preferably Y is lysine in formula (I).
Preferably Y is glutamic acid in formula (II).
Preferably $q$ is 1 to 5.
Preferably $n$ is 2.

The present invention also provides a fibre-shaping peptide having the sequence:
(NH$_3$-KIRRLKQKNARLK($\beta$A)$_3$)$_2$-K The present invention also provides a fibre-shaping peptide having the sequence:
E-(($\beta$A)$_3$EIAALEYEIAALEQ-COOH)$_2$ $\beta$A as used in the above sequences represents $\beta$-alanine.

The present invention also provides a protein structure comprising the fibre-shaping peptide of the present invention.

Preferably the protein structure comprises a plurality of fibre-shaping peptides according to the present invention and a plurality of self-assembling peptides as defined above which can self-assemble to form a linear protein structure, wherein the fibre-shaping peptides and the self-assembling peptides self-assemble to form a protein structure.

As will be appreciated by those skilled in the art, in order to form a protein structure the plurality for self-assembling peptides will comprise a first set of self-assembling and a second set of self-assembly fibres which interact to form a substantially linear structure. Preferably, the ratio of fibre-shaping peptides: first self-assembly peptides: second self-assembly peptides comprised in the protein structure of the present invention is from about $1\times10^{-6}$:1:1 to 10:1:1, more preferably from about $1\times10^{-4}$:1:1 to 2:1:1.

The term "protein structure" refers to any combination of secondary protein structures, such as helices and $\beta$ strands. It is particularly preferred that the protein structure is or comprises one or more protein fibres, wherein the protein fibres are as defined above.

Preferably the protein structure of the present invention comprises kinked and waved fibres.

Preferably the protein structure of the present invention comprises split and branched fibres.

The present invention also provides a method for producing the protein structure of the present invention, comprising mixing a plurality of fibre-shaping peptides of the present invention and a plurality of self-assembling peptides under conditions so that the peptides associate to form a protein structure.

Suitable conditions for forming a protein structure by mixing the peptides will be apparent to those skilled in the art, especially in view of the information given in WO 01/21646.

The present invention also provides a kit for producing the protein structure of the present invention, wherein the kit comprises a plurality of the fibre-shaping peptides of the present invention and a plurality of self-assembling peptides, wherein the fibre-shaping peptides and the self-assembling peptides can associate to form a protein structure.

By controlling the amount of fibre-shaping peptides in the protein structure, the morphology of the protein structure can be changed. Accordingly, it is possible to have some control over the protein structures being generated. In particular, protein fibres can be arranged to form 2 and 3 dimensional assemblies such as grids, scaffolds, filters, networks and matrices. Such protein structures can be used in a number of applications such as in the purification of biological fluids such as blood, or the assembly of cells for cell and tissue engineering purposes. The protein structures may also be used for surface engineering (see Zhang et al., Biomaterials, 16, 1385-1393, 1995).

Furthermore, as the fibre-shaping peptides can comprise functional molecules the protein structure can be functionalised. For example, if the functional molecules are capable of specifically binding a desired component or contaminant, the matrix can be used as an affinity matrix for isolating a desired component or for removing a contaminant. For example in the case of virus removal from a blood sample, a binder for the target contaminant (e.g. a peptide or protein with natural or engineered affinities for a viral coat protein) is the functional molecule attached to the fibre-shaping peptide. The matrix can then be removed from blood along with any bound contaminants by light centrifugation.

The protein structures of the present application have a number of other applications including:
i. preparation of organised networks for seeding the crystalisation of biomolecules for X-ray crystallography;
ii. using protein structures to promote cell growth for tissue engineering;
iii. the construction of nanoscale molecular sieves and other devices;
iv. the preparation of nanoscale molecular grids/scaffolds that could be used as supports for a variety of functional molecules;
v. functionalised protein structures could be used in, for example, catalysis, affinity-sieving/purification of biological fluids and other research solutions, the recruitment of endogenous molecules and co-factors to promote tissue repair and tissue engineering in general.

Although the fibre-shaping peptide of the present invention may comprise one or more functional molecules, additional functional molecules can be attached to the protein structure of the present invention at any appropriate site using standard coupling techniques.

BRIEF DESCRIPTION OF THE DRAWINGS

The present invention is now described, by way of example only, with reference to the accompanying Figures.

FIG. 3 shows the results of an analysis of the morphological changes introduced into the self-assembling fibres: a, shows the average number of features (kinks or splits) per 10 μm length of fibres. b, shows the average length of the mature fibres as functions of the ratio of FiSh to SAF peptides. Data points for $CC^{NN}$-containing fibres are shown as circles, whereas those for $DD^{CC}$-containing fibres are shown as squares. In panel a the numbers of kinks and splits produced by $DD^{CC}$ are distinguished by solid and broken lines, respectively. Analysis: the numbers given are averages measured over 80-100 fibres. Standard deviations on the measurements in a were: 2.6 (for 0.01:1:1) and 0.2 (for <0.01:1:1) for the $CC^{NN}$-containing fibres; 0.4 (for 0.01:1:1) and 0.1 (for <0.01:1:1) for the $DD^{CC}$-containing split fibres, and 0.4 (for 0.01:1:1) and 0.1 for (>0.01:1:1) for the kinked fibres. Standard deviations on the measurements in b were 5.6 μm (for 0.01:1:1) and 1.6 μm (for >0.01:1:1) for data from both FiSh peptides.

EXAMPLES

Materials and Methods

Peptide Synthesis

Figure 1:
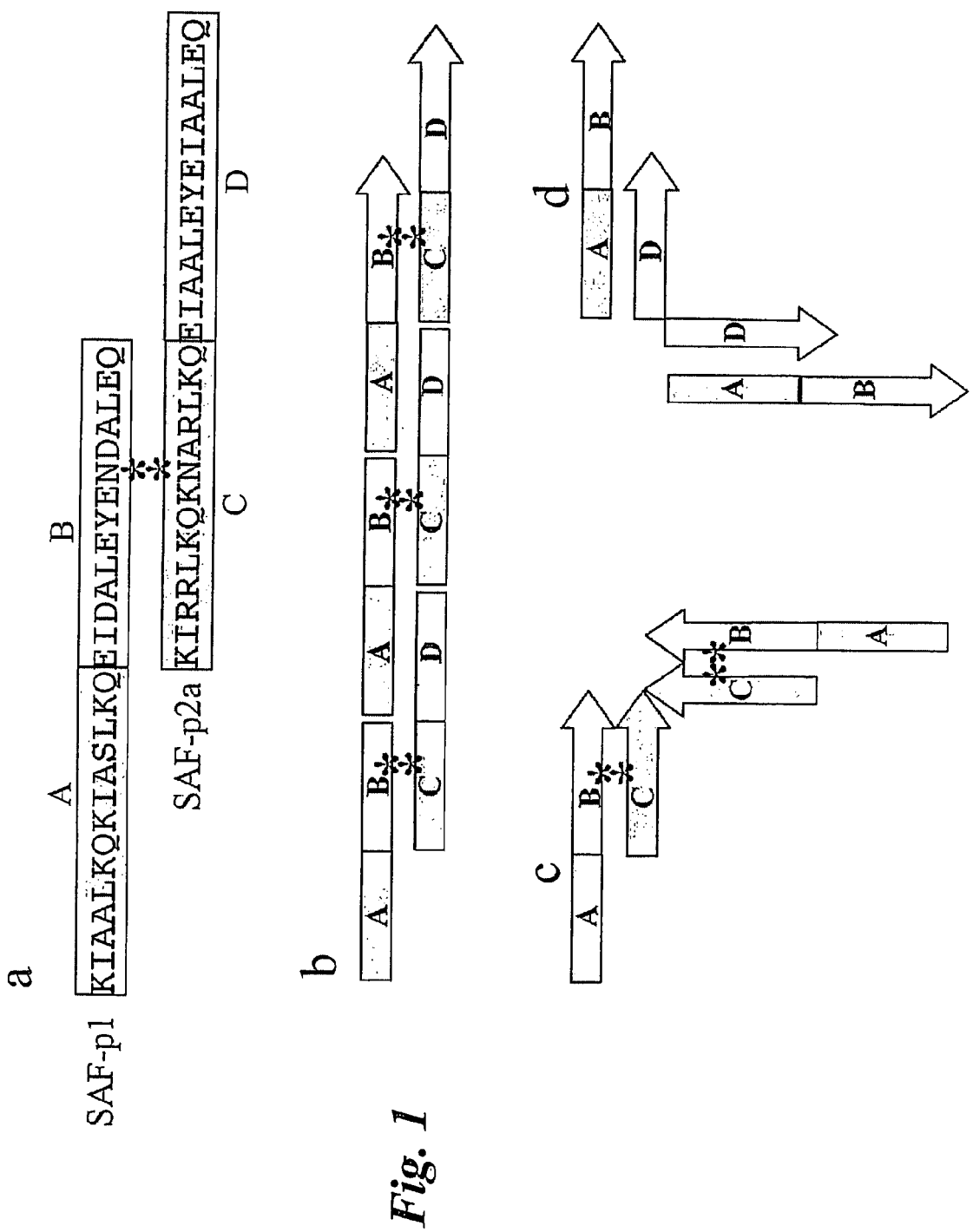
FIG. 1 illustrates the design principles and sequences for the self-assembling fibre (SAF) and fibre-shaping (FiSh) peptides: a. The standard SAF peptide sequences each shown divided into two blocks: A and B for SAF-p1; C and D for SAF-p2a. a & b. Block A complements D and B complements C. This leads to sticky-ended dimers that assemble further into fibres. The register of the assembly is partly maintained by the key asparagine residues highlighted by the asterisks. c & d, The discontinuities designed to be introduced by the FiSh peptides CC$^{NN}$ and DD$^{CC}$, respectively. In b, c & d, the direction of the polypeptide chain (N- to the C-termini) is shown by the arrowheads. This relates to the nomenclature of the FiSh peptides; for example, CC$^{NN}$ is so-named because it comprises two copies of the block C from SAF-p2a linked through their C-termini, which leaves both N-termini free at the ends of the construct. The FiSh peptides are shown kinked rather than straight as the linkers contain flexible b-alanine residues.

Peptides were synthesized using standard solid-phase Fmoc chemistry, purified by RP-HPLC and confirmed by MALDI-TOF mass spectrometry.

Fibre Assembly

All samples of fibres were prepared with SAF-p1 and SAF-p2a (each at 100 μM concentration) with the designated amounts of FiSh peptides, and incubated at 22° C. overnight following the techniques described in Pandya et al., 2000 (supra).

Electron Microscopy

Fibre suspensions were dried onto carbon grids and stained with uranyl acetate for electron microscopy as described previously in Pandya et al., 2000 (supra).

Recruitment of Gold Particles

Streptavidin nanogold conjugate (streptavidin labeled with colloidal gold nanoparticles (5 or 10 nm)) were obtained from SIGMA. All the peptide synthesis reagents including biotinylated Fmoc-lysine were purchased from Merck Biosciences (Novabiochem). Peptides were synthesized on a Pioneer Peptide Synthesis System using standard Fmoc-chemistry as described above.

The streptavidin nanogold conjugate (SNC) was 2-10 times diluted with 10 mM MOPS, pH 7 as the diluent buffer containing 0.05% TWEEN 20 to minimise background. The diluted conjugate was allowed to equilibrate for 30 min in this lower glycerol content at room temperature. The optimal concentration was determined empirically (in accordance with the procedure recommended by SIGMA) to be $A_{520}$=0.25 with incubation time 30-45 minutes.

Fibre samples were prepared as indicated above (except biotinylated Fmoc-lysine was used to incorporate biotin into the peptides). A commercial Fmoc-lysine which had biotin attached the side-chain (epsilon) amino group was used to biotin into the synthesis of both straight and fibre shaping peptides. For straight peptides standard linear synthesis was used. Fibre shaping peptides incorporating biotin were created using a di-lysine hub, that is Lys-Lys (biotin). The first lysine acted as the hub from which the two peptide arms were grown. The alpha and epsilon amino acid groups of this lysine were used to initiate peptide synthesis. The alpha carboxy group of the first lysine was coupled to the second lysine, which contained the biotin. A designated amount (2 μL) of SNC was then added to the fibre preparations. To achieve better coverage of fibre surfaces with SNC in some applications either higher volumes (up to 20 μL) or concentrations (up to 2 times dilution) were used.

After incubation an 8 μL drop of peptide solution was applied to a carbon-coated copper specimen grid (Agar Scientific Ltd) and dried with filter paper followed by washing two-three times (3-5 min each) with standard MOPS buffer to eliminate unspecifically bound SNC. The grid was stained with filtered 0.5% aqueous uranyl acetate for electron microscopy at 20° C.

The novel protein structures described herein were made by combining SAF-p1 and SAF-p2a in the presence of fibre-shaping peptides based on the SAF-p2a sequence following the technique described in Pandya et al., 2000 (supra).

The present invention is demonstrated, by way of example only, with two novel peptides, $CC^{NN}$ and $DD^{CC}$, which introduce kinks/waves and splits/branches into the SAF fibres, respectively.

The design principles for $CC^{NN}$ and $DD^{CC}$ peptides are shown schematically in FIGS. 1c&d. The peptides were based on the SAF-p2a sequence, FIG. 1a. For example, in $CC^{NN}$ the N-terminal "C" subunit of SAF-p2a was duplicated in a tail-to-tail fashion; i.e., two copies of the C sequence (hence the "CC" term) were linked through their C-termini leaving the N-termini free at the ends of the construct (hence the "NN" superscript). This was achieved by synthesising two C subunits simultaneously from the two amino groups of a single, bifunctional hub, namely L-lysine attached via its carboxy terminus to a solid-phase peptide synthesis resin. To allow additional flexibility at the lysine joint, three β-alanine monomers were added to the amino groups of the lysine prior to synthesis of the C sequences. As depicted in FIG. 1c, this should set up the possibility for $CC^{NN}$ to interact with two copies of SAF-p1. However, this interaction is altogether different from the interaction originally prescribed for the self-assembling peptides (straights), SAF-p2a and SAF-p1: the association of these is parallel and contiguous, FIGS. 1a&b, which leads to linear and potentially infinite assemblies (Pandya et al., Biochemistry, 39, 8728-8734, 2000); in contrast, the addition of $CC^{NN}$ aimed to force two neighbouring SAF-p1 peptides to converge; the reason for including the β-alanine linker was thus to accommodate any resulting discontinuity and, so, effectively allow fibrillogensis from the two SAF-p1 peptides, FIG. 1c. Similar principles were used in the $DD^{CC}$ design except that two copies of the D subunit of SAF-p2a were linked through their N-termini using L-glutamic acid as a hub, FIG. 1d; again three β-alanine residues were used to separate each of the D peptide sequences from the hub. There are subtle differences in the sequences of the C and D units, FIG. 1a, which, as discussed below, resulted in different morphological changes in the SAF assemblies.

Figure 2:
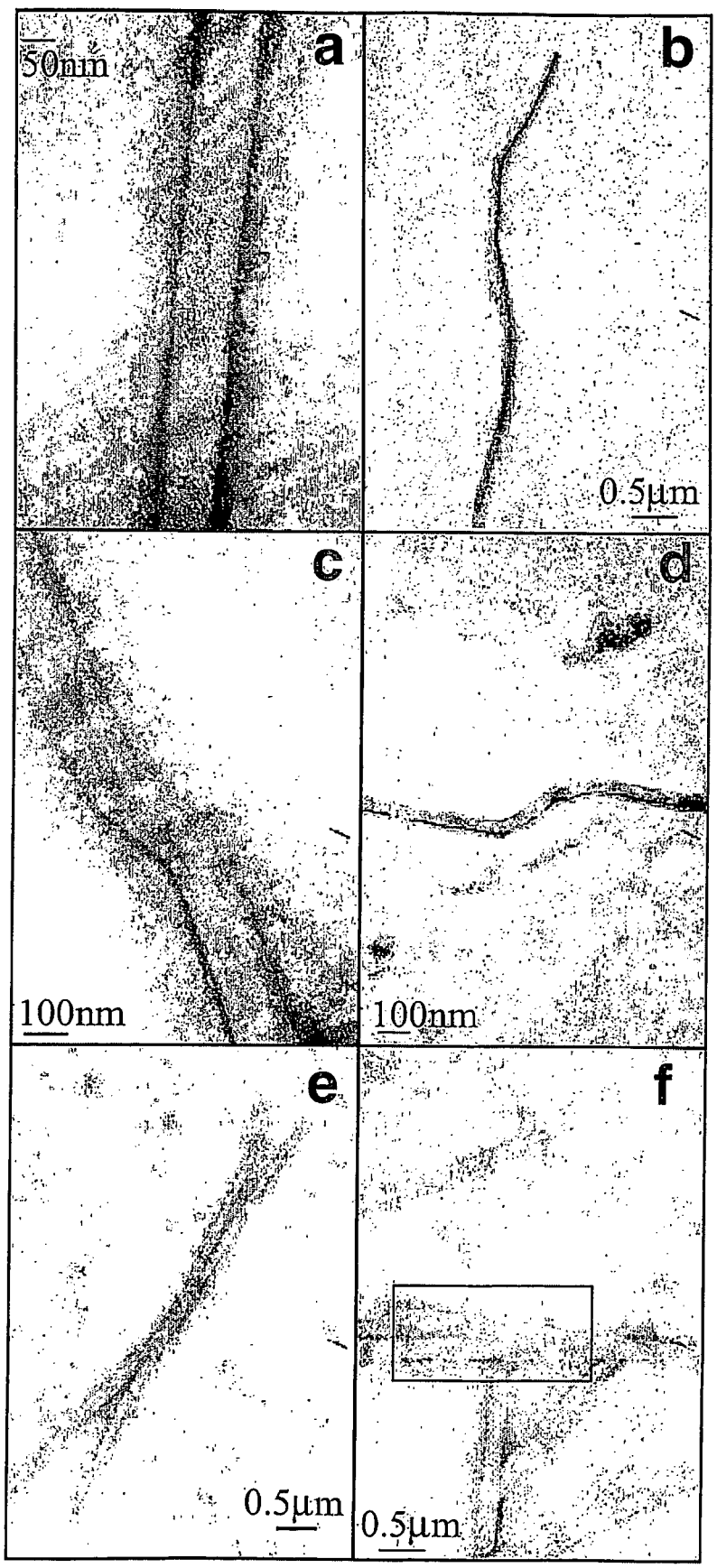
FIG. 2 shows uranyl-acetate stained TEM images of fibres formed from the SAF and SAF-FiSh systems. a, straight fibres formed from mixing SAF-p1 and SAF-p2a in a 1:1 ratio. b-d, kinked and waved fibres formed by adding the $CC^{NN}$ FiSh peptide to fresh SAF-p1/SAF-p2a mixtures in 1:1:1 (b), 0.1:1:1 (c), and <0.1:1:1 (d) (FiSh:SAF-p1:SAF-p2a) ratios. e&f, split and branched (bounded by the box in f) fibres formed by adding the $DD^{CC}$ FiSh peptide to fresh SAF-p1/SAF-p2a mixtures in 0.01:1:1 ratios.

Consistent with the design, when $CC^{NN}$ was doped into a fresh SAF-p1/SAF-p2a mixture the resulting matured fibres were not straight, but kinked or wavy, FIGS. 2b,c&d. Varying the ratio of $CC^{NN}$ in the starting mixtures altered the numbers of kinks per unit length of fibres, FIG. 3a. However, this was at the expense of fibre integrity: the inclusion of more $CC^{NN}$ reduced the length of the fibres that were formed, FIG. 3b. Though some linear fibres were observed these were rare, and the number reduced rapidly with increasing amounts of $CC^{NN}$.

Figure 4:
FIG. 4 shows transmission electron microscopy images of the original SAF-p1:SAF-p2-based fibres without (a) and with (b) $CC^{NN}$.

Though these observations are consistent with the design of the $CC^{NN}$ FiSh peptide, it is perhaps surprising that the kinked fibres appear so rigid. It is probable that the aforementioned thickening of the fibres stabilizes them and thus limits kinking. To test this, we prepared samples of the original SAF-p1:SAF-p2 design without $CC^{NN}$; note that the coiled-coil interfaces of original and redesigned SAF peptides and the FiSh peptides were unaltered, and so remained compatible. The sequence of SAF-p2 is KIRALKAKNAHLLKQE-IAALEQEIAALEQ, which differs at four residues from SAF-p2a. SAF-p2 combines with SAF-p1 to give fibres that are approximately two thirds the diameter of the redesigned SAF-p1:SAF-p2a fibres, and are less stable to heat (A. M. Smith & D. N. Woolfson, unpublished results). Samples were prepared by incubating SAF-p1 and SAF-p2 with or without $CC^{NN}$ (each peptide was at 100 μM concentration) at 5° C. for 1 hour before the standard preparation for electron microscopy. Without $CC^{NN}$, SAF-p1+SAF-p2 produced extended linear fibres, FIG. 4a, but with the FiSh peptide multiple kinks were apparent, FIG. 4b. The extent and frequency of kinking in the SAF-p1:SAF-p2 background was greater than that observed with SAF-p1+SAF-p2a. This suggests that the flexibility of the SAF plays a role in kinking: the thinner, less-stable SAF-p1:SAF-p2 fibres contain more kinks. Consistent with this, the fibre shortening observed for FiSh peptides in the redesigned SAF-p1:SAF-p2a background, FIG. 3b, was less apparent in the original SAF-p1:SAF-p2 background, FIG. 4.

Intriguingly, inclusion of $DD^{CC}$ in fresh SAF-p1/SAF-p2a mixtures led to two different morphologies in the matured fibres: with small amounts of the FiSh peptide (101:1:1 of $DD^{CC}$:SAF-p1:SAF-p2a) the fibres kinked as observed with $CC^{NN}$. However, as the ratio of $DD_{CC}$ was increased (up to 1:1:1) less kinking was observed, and instead the fibres tended to split or branch, FIGS. 2e&f and FIG. 3a.

The difference in behaviour of the two FiSh peptides must result from the different sequences of the C and the D subunits, FIG. 1a. In the original SAF design, the C subunit of SAF-p2 was made to partner the B subunit of SAF-p1 specifically by the inclusion of complementary asparagine residues in each of the peptides at a key interfacial site (Pandya et al., Biochemistry, 39, 8728-8734, 2000); this feature was preserved in the SAF-p2a design. This is a so-called negative-design principle (Beasley et al., J. Biol. Chem., 277, 10150-10155, 2002); that is, it is a feature incorporated to direct the assembly of one structure and guard against the formation of potential alternatives. In the case of the SAFs, the asparagine residues were included to ensure parallel heterodimer formation (Harbury et al., Science, 262, 1401-1407, 1993, O'Shea et al., Curr. Biol., 3, 658-667, 1993, Woolfson et al., Prot. Sci., 4, 1596-1607, 1995, O'Shea et al., Science, 254, 539-44, 1991, Lumb et al., Biochemistry, 34, 8642-8648, 1995 and Gonzalez et al., Nature Struct. Biol., 3, 1011-1018, 1996) to offset the register of the two peptides and hence to promote fibrillogenesis (Pandya et al., Biochemistry, 33, 8728-8734, 2000). Although the inclusion of asparagine increases dimer and register specificity in leucine-zipper peptides this is at the expense of overall stability (Harbury et al., Science, 262, 1401-1407, 1993, Lumb et al., Biochemistry, 34 8642-8648, 1995 and Gonzalez et al., Nature Struct. Biol., 3, 1011-1018, 1996). The $CC^{NN}$ peptide has two such asparagines and the $DD^{CC}$ has none. Therefore, the inventors suspect that the $DD^{CC}$ forms stronger leucine-zipper interactions and is potentially the more promiscuous in its interactions with the standard SAF peptides, and that this leads to split and/or thickened appearance of some of the fibres, FIGS. 2e&f. Put another way, $CC^{NN}$ is more selective in the interactions it makes. This, combined with the presumed lower stability of B:C interactions compared with A:D interactions, leads to fewer and more-easily rectified imperfections (such as splitting and thickening).

Following the scheme of FIG. 1, there are sixteen possible combinations of the C and D subunits of SAF-p2a. We synthesised two of these, $CD^{NC}$ and $CC^{NC}$, as control peptides. $CD^{NC}$ was simply the SAF-p2a sequence with a spacer inserted between the C and D subunits; in $CC^{NC}$ two successive copies of C were separated by the spacer; in both cases the spacer comprised three β-alanine residues, a central ε-aminohexanoic acid residue (as a substitute for the L-lysine and L-glutamic acid hubs used in $CC^{NN}$ and $DD^{CC}$), followed by three further β-alanine residues. Neither $CD^{NC}$ nor $CC^{NC}$ caused kinking, waving, splitting or branching of the matured fibres as observed for $CC^{NN}$ and $DD^{CC}$. However, at ratios of $10^{-2}$:1:1 (control:SAF-p1:SAF-p2a) and above, both $CD^{NC}$ and $CC^{NC}$ inhibited fibre assembly completely; mixtures with smaller amounts of control peptide did produce fibres, but these were short (<20 mm) and rare (500 times less abundant than in mixtures containing the FiSh peptides $CC^{NN}$ and $DD^{CC}$). In other words, $CD^{NC}$ and $CC^{NC}$ acted as terminators in fibrillogenesis.

In summary, the inventors have presented experimental data for altering the shapes of designed self-assembly fibres that originally formed exclusively linear and non-branched structures. Fibre-shaping (FiSh) peptides were added to mixtures of peptides that would otherwise have formed linear assemblies. The two FiSh peptides tested influenced fibres morphology differently: one kinked the fibres, whereas the other split, or branched them. The ratio of FiSh to standards peptide determined the number of kinked and branched features observed.

The ability to alter fibre morphologies can be used in the development of biomaterials that respond to cues provided by their environment. Such cues might be presented as a pattern on a surface. This could lead to surfaces functionalised with proteins for the applications in protein-array technology and the development of new protein-based diagnostic/sensor devices. Another possibility is for the assembly of networks that might be used as scaffolds in cell and tissue engineering. In this case the self-assembly fibres could be induced to respond to, and so support cell growth.

As indicated above, as the FiSh peptides may comprise other functional molecules. In this way the FiSh peptides could be used to recruit bioactive peptides, proteins and small molecules to assembled fibres. For example, the additional moiety could be a peptide antigen, which once incorporated into the fibre could be used to pull-down (i.e. recruit) a specific antibody to the fibre surface. Alternatively, if the functional molecule is a nucleic acid sequence, transcription factors that interact with the nucleic acid sequence may be isolated. In these respects, the FiSh peptides should be considered as nodes at which functional groups could be located.

Figure 6:
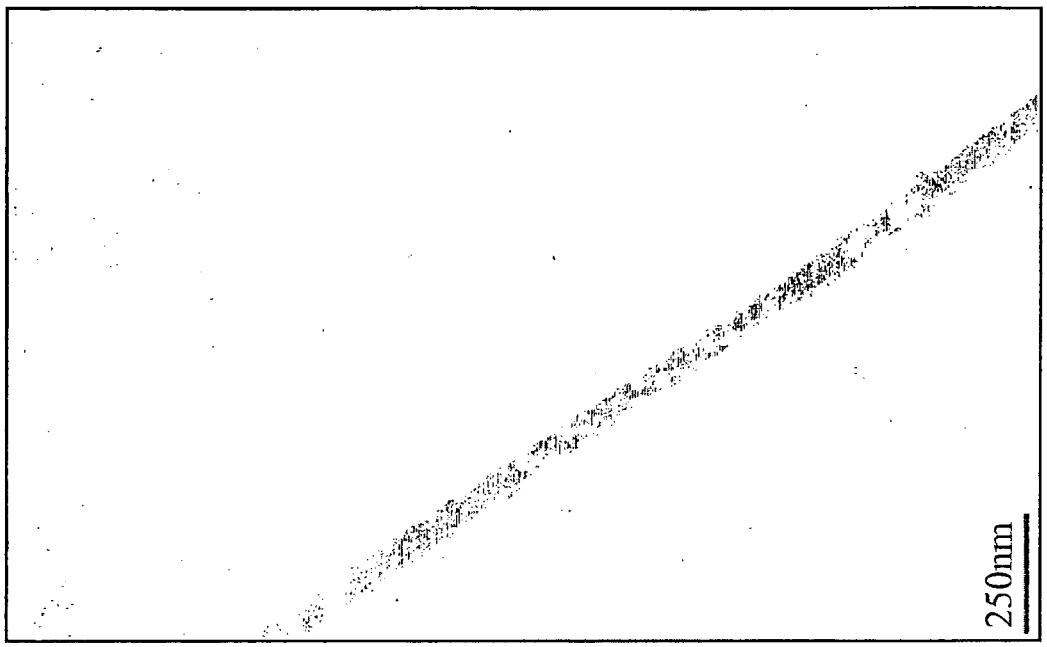
FIG. 6 shows a transmission electron microscopy image of a single straight peptide fibre having recruited gold peptides via streptavidin, which in turn was recruited to the fibres by biotin incorporated into the self-assembling peptides.
Figure 5:
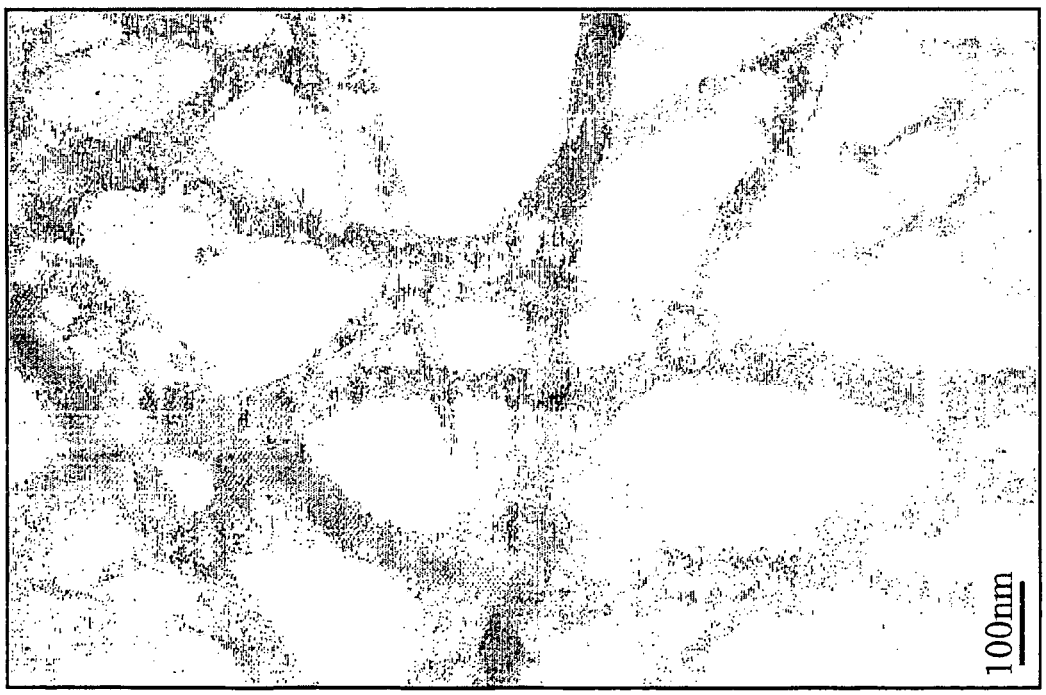
FIG. 5 shows a transmission electron microscopy image of a straight peptide fibre matrix having recruited gold peptides via streptavidin, which in turn was recruited to the fibres by biotin incorporated into the self-assembling peptides.
Figure 8:
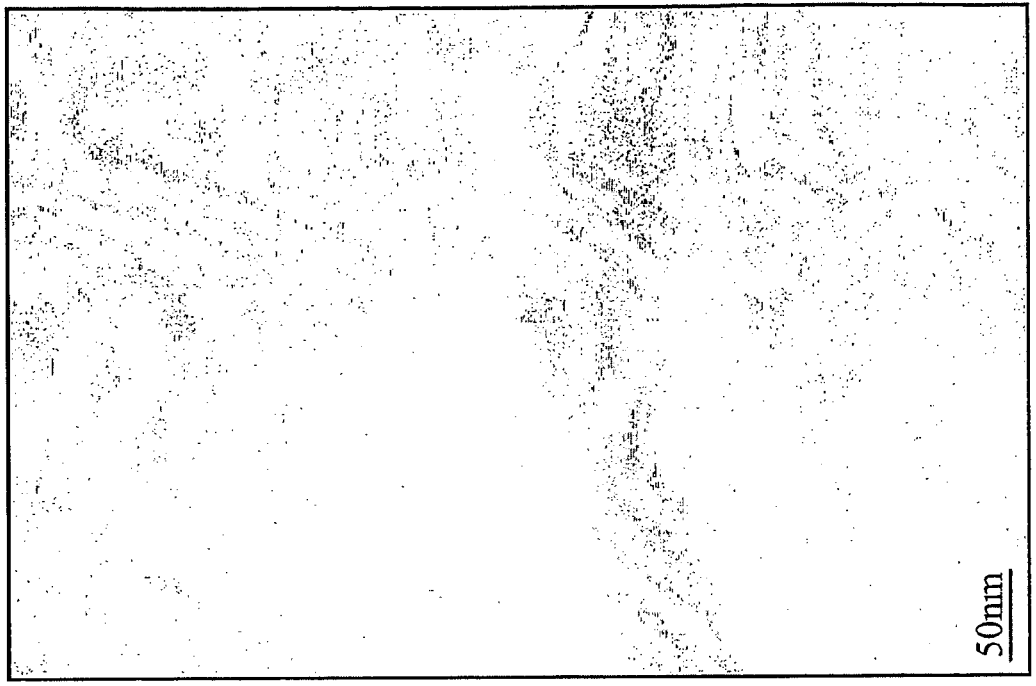
FIG. 8 shows a transmission electron microscopy image of a kinked peptide fibre having a gold particle specifically recruited at the hub of the particle.
Figure 7:
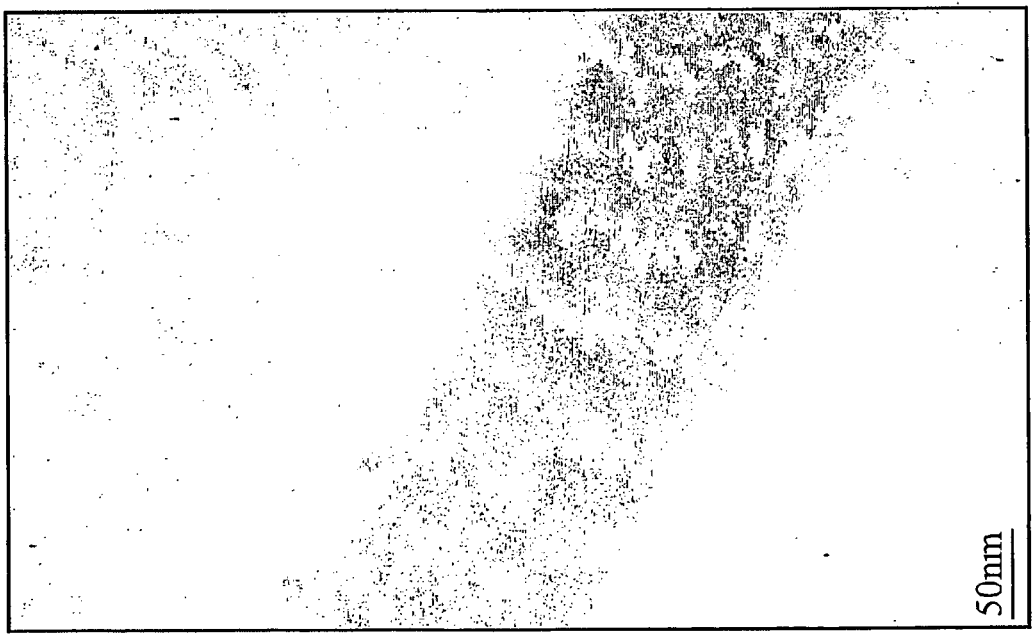
FIG. 7 shows a high magnification transmission electron microscopy image of a single straight peptide fibre having recruited gold peptides via streptavidin, which in turn was recruited to the fibres by biotin incorporated into the self-assembling peptides.

10 nm gold particles were recruited to both straight fibres and the kinked fibres of the present invention using standard biotin/streptavidin chemistry as described above. In particular, biotin was incorporated into the self-assembling peptides during synthesis and the gold particles were coated with streptavidin. It was found that the gold particles were randomly distributed on the straight fibres (see FIGS. 5 to 7) but were specifically recruited at the hub of the kinked fibres (see FIG. 8).

In the straight fibres one of the amino acids in the "f" position of the heptad was derivatised with biotin. In the kinked fibre the hub was derivatised with biotin. It is advantageous to be able to specifically recruit functional molecules such as gold particles to specific sites within the kinked fibres of the present invention.

All documents cited above, are incorporated herein by reference.

The invention claimed is:

1. A fibre-shaping peptide comprising:
   (i) a polypeptide according to SEQ ID NO: 3 with a first and optionally a second peptide monomer unit according to SEQ ID NO: 9 attached to the lysine residue shown at position 17 of SEQ ID NO: 3, wherein the first peptide monomer unit is attached via an amide bond to epsilon amino group of the lysine residue, and the optional second peptide monomer unit is attached to the lysine residue via carboxyl group of the lysine residue; or
   (ii) a polypeptide according to SEQ ID NO: 5 with a first and optionally a second peptide monomer unit according to SEQ ID NO: 10 attached to the glutamic acid residue shown at position 1 of SEQ ID NO: 5, wherein said first peptide monomer unit is attached to the glutamic acid residue via an amide bond to a carboxylic acid group of the glutamic acid residue, and the optional second peptide monomer unit is attached via an amide bond to amino group of said glutamic acid residue.

2. The fibre-shaping peptide according to claim 1, which additionally comprises one or more functional molecules attached to the lysine residue of (i) or the glutamic acid residue of (ii).

3. The fibre-shaping peptide according to claim 2, wherein the functional molecule is an antibody molecule, a receptor, a ligand, an enzyme, an antigen, a label, a metal ion or a nucleic acid molecule.

4. The fibre-shaping peptide according to claim 2, wherein the functional molecule is attached to the lysine residue of (i) or the glutamic acid residue of (ii) via a second flexible linker.

5. The fibre-shaping peptide according to claim 4, wherein the second flexible linker is a peptide linker comprising amino acids selected from the group consisting of glycine, alanine, serine and β-alanine.

6. The fibre-shaping peptide according to claim 4, wherein the second flexible linker is a poly-β-alanine peptide.

7. A fibre-shaping peptide comprising:
   a polypeptide according to SEQ ID NO: 3 with a first and optionally a second peptide monomer unit according to SEQ ID NO: 9 attached to the lysine residue shown at position 17 of SEQ ID NO: 3, wherein the first peptide monomer unit is attached via an amide bond to epsilon amino group of the lysine residue, and the optional second peptide monomer unit is attached to the lysine residue via carboxyl group of the lysine residue;

8. A fibre-shaping peptide comprising:
   a polypeptide according to SEQ ID NO: 5 with a first and optionally a second peptide monomer unit according to SEQ ID NO: 10 attached to the glutamic acid residue shown at position 1 of SEQ ID NO: 5, wherein said first peptide monomer unit is attached to the glutamic acid residue via an amide bond to a carboxylic acid group of the glutamic acid residue, and the optional second peptide monomer unit is attached via an amide bond to amino group of said glutamic acid residue.

9. The fibre-shaping peptide according to claim 8, which additionally comprises one or more functional molecules attached to the glutamic acid residue.

10. The fibre-shaping peptide according to claim 9, wherein the functional molecule is an antibody molecule, a receptor, a ligand, an enzyme, an antigen, a label, a metal ion or a nucleic acid molecule.

11. The fibre-shaping peptide according to claim 9, wherein the functional molecule is attached to the glutamic acid residue via a second flexible linker.

12. The fibre-shaping peptide according to claim 11, wherein the second flexible linker is a peptide linker comprising amino acids selected from the group consisting of glycine, alanine, seine and β-alanine.

13. The fibre-shaping peptide according to claim 11, wherein the second flexible linker is a poly-β-alanine peptide.

14. The fibre-shaping peptide according to claim 7, which additionally comprises one or more functional molecules attached to the lysine residue.

15. The fibre-shaping peptide according to claim 14, wherein the functional molecule is an antibody molecule, a receptor, a ligand, an enzyme, an antigen, a label, a metal ion or a nucleic acid molecule.

16. The fibre-shaping peptide according to claim 14, wherein the functional molecule is attached to the lysine residue via a second flexible linker.

17. The fibre-shaping peptide according to claim 16, wherein the second flexible linker is a peptide linker comprising amino acids selected from the group consisting of glycine, alanine, serine and β-alanine.

18. The fibre-shaping peptide according to claim 16, wherein the second flexible linker is a poly-β-alanine peptide.

* * * * *

UNITED STATES PATENT AND TRADEMARK OFFICE
CERTIFICATE OF CORRECTION

PATENT NO.        : 7,507,790 B2                                    Page 1 of 1
APPLICATION NO.   : 10/526367
DATED             : March 24, 2009
INVENTOR(S)       : Derek Woolfson et al.

It is certified that error appears in the above-identified patent and that said Letters Patent is hereby corrected as shown below:

In Column 17, Claim 12, Line 7:
    Please delete "seine" and insert --serine--.

Signed and Sealed this

Sixth Day of October, 2009

David J. Kappos
*Director of the United States Patent and Trademark Office*